United States Patent
Gill et al.

(10) Patent No.: US 7,970,551 B2
(45) Date of Patent: Jun. 28, 2011

(54) ANALYSIS OF DNA

(75) Inventors: Peter Gill, Birmingham (GB); Amanda Kirkham, Birmingham (GB)

(73) Assignee: Forensic Science Service Limited, Birmingham (GB)

( * ) Notice: Subject to any disclaimer, the term of this patent is extended or adjusted under 35 U.S.C. 154(b) by 0 days.

(21) Appl. No.: 12/686,174

(22) Filed: Jan. 12, 2010

(65) Prior Publication Data

US 2010/0114500 A1     May 6, 2010

Related U.S. Application Data

(62) Division of application No. 10/564,682, filed as application No. PCT/GB2004/003003 on Jul. 9, 2004, now Pat. No. 7,668,660.

(30) Foreign Application Priority Data

Jul. 15, 2003  (GB) .................................. 0316519.8

(51) Int. Cl.
    *G01N 33/48*     (2006.01)
(52) U.S. Cl. ......................................................... 702/19
(58) Field of Classification Search ..................... 702/19, 702/20, 22, 27
    See application file for complete search history.

(56) References Cited

U.S. PATENT DOCUMENTS

2002/0007248 A1  1/2002  Gill et al.
2006/0281134 A1  12/2006  Love

OTHER PUBLICATIONS

Gill, P. et al. "Development of a Simulation Model to Assess the Impact of Contamination in Casework Using STRs," Journal of Forensic Sciences, 49(3):485-491, May 2004.
Gill, P. "Role of Short Tandem Repeat DNA in Forensic Casework in the UK-Past, Present, and Future Perspectives," Biotechniques, 32(2):366-385, Feb. 2002.
Gill, P. et al. "An investigation of the rigor of interpretation rules for STRs derived from less than 100 pg of DNA," Forensic Science International, 112(1):17-40, Jul. 2000.
Rutty, G. et al. "DNA contamination of mortuary instruments and work surfaces: a significant problem in forensic practice?" International Journal of Legal Medicine, 114(1-2):56-60, Dec. 2000.

*Primary Examiner* — Drew A Dunn
*Assistant Examiner* — Stephen J Cherry
(74) *Attorney, Agent, or Firm* — Merchant & Gould P.C.

(57) ABSTRACT

The invention provides methods for providing information on the probability of DNA samples being contaminated over days, weeks and months in relation to collection, processing and analysis of DNA samples. Methods are also provided for analyzing the likelihood of a result arising due to contamination and/or determining the analysis protocol to be applied to a DNA sample and/or methods of operating databases, particularly containing DNA profiles.
Improvements in accounting for sporadic and undetected contamination and improvements in the operation of DNA sampling of analysis are provided by the invention.

30 Claims, 6 Drawing Sheets

| Sum peak height | no. alleles | | | | | Sample no. |
|---|---|---|---|---|---|---|
| | >0rfu | >25rfu | >50rfu | >100rfu | >150rfu | |
| 0 | 0 | 0 | 0 | 0 | 0 | 5 |
| 0 | 0 | 0 | 0 | 0 | 0 | 10 |
| 0 | 0 | 0 | 0 | 0 | 0 | 38 |
| 0 | 0 | 0 | 0 | 0 | 0 | 44 |
| 0 | 0 | 0 | 0 | 0 | 0 | 49 |
| 54 | 1 | 1 | 1 | 0 | 0 | 23 |
| 142 | 2 | 2 | 2 | 0 | 0 | 30 |
| 424 | 4 | 4 | 4 | 3 | 1 | 29 |
| 763 | 5 | 5 | 5 | 3 | 3 | 47 |
| 1310 | 7 | 7 | 7 | 3 | 3 | 32 |
| 1556 | 13 | 13 | 13 | 7 | 2 | 31 |
| 1595 | 13 | 13 | 13 | 8 | 4 | 14 |
| 1644 | 16 | 16 | 16 | 6 | 3 | 9 |
| 1784 | 13 | 13 | 13 | 10 | 5 | 42 |
| 1784 | 13 | 13 | 13 | 10 | 5 | 50 |
| 1908 | 14 | 14 | 14 | 9 | 7 | 15 |
| 2686 | 10 | 10 | 10 | 9 | 9 | 39 |
| 3806 | 17 | 17 | 17 | 15 | 14 | 4 |
| 3970 | 19 | 19 | 19 | 16 | 14 | 8 |
| 4016 | 19 | 19 | 19 | 15 | 12 | 35 |
| 4126 | 22 | 22 | 22 | 21 | 19 | 12 |
| 4161 | 19 | 19 | 19 | 19 | 19 | 22 |
| 4509 | 12 | 12 | 12 | 9 | 8 | 17 |
| 5001 | 14 | 14 | 14 | 14 | 14 | 34 |
| 7255 | 16 | 16 | 16 | 16 | 16 | 13 |
| 7917 | 21 | 21 | 21 | 21 | 21 | 45 |
| 7988 | 18 | 18 | 18 | 18 | 18 | 41 |
| 8250 | 18 | 18 | 18 | 16 | 16 | 43 |
| 8303 | 22 | 22 | 22 | 20 | 19 | 7 |
| 8512 | 15 | 15 | 15 | 15 | 15 | 26 |
| 9522 | 20 | 20 | 20 | 20 | 20 | 2 |
| 11304 | 20 | 20 | 20 | 20 | 20 | 40 |
| 11346 | 21 | 21 | 21 | 21 | 21 | 46 |
| 11689 | 19 | 19 | 19 | 19 | 19 | 27 |
| 13219 | 20 | 20 | 20 | 20 | 20 | 16 |
| 15011 | 20 | 20 | 20 | 20 | 20 | 11 |
| 15771 | 18 | 18 | 18 | 18 | 18 | 24 |
| 16919 | 20 | 20 | 20 | 20 | 20 | 37 |
| 17805 | 20 | 20 | 20 | 20 | 19 | 18 |
| 18387 | 22 | 22 | 22 | 22 | 22 | 33 |
| 21198 | 22 | 22 | 22 | 22 | 22 | 48 |
| 22353 | 20 | 20 | 20 | 20 | 20 | 3 |
| 25086 | 19 | 19 | 19 | 19 | 19 | 25 |
| 27543 | 21 | 21 | 21 | 21 | 21 | 6 |
| 36804 | 18 | 18 | 18 | 18 | 18 | 19 |
| 40367 | 19 | 19 | 19 | 19 | 19 | 20 |
| 41817 | 20 | 20 | 20 | 20 | 20 | 28 |
| 42273 | 21 | 21 | 21 | 21 | 21 | 1 |
| 45110 | 19 | 19 | 19 | 19 | 19 | 21 |
| 73211 | 21 | 21 | 21 | 21 | 21 | 36 |

Table 1: Case samples ranked in order of increasing summed peak height with numbers of alleles scored above a given peak height.

FIG. 3

| Sum peak height | >0 | >25 | >50 | >100 | no. alleles >150 | >200 | >250 | Sample no. |
|---|---|---|---|---|---|---|---|---|
| 1217 | 16 | 16 | 16 | 5 | 3 | 0 | 0 | 26 |
| 1109 | 17 | 17 | 9 | 4 | 2 | 2 | 1 | 15 |
| 695 | 11 | 10 | 6 | 1 | 1 | 1 | 1 | 3 |
| 481 | 11 | 11 | 3 | 0 | 0 | 0 | 0 | 16 |
| 413 | 8 | 6 | 2 | 2 | 1 | 0 | 0 | 1 |
| 334 | 10 | 9 | 0 | 0 | 0 | 0 | 0 | 8 |
| 290 | 7 | 6 | 2 | 0 | 0 | 0 | 0 | 14 |
| 242 | 7 | 5 | 1 | 0 | 0 | 0 | 0 | 4 |
| 234 | 5 | 4 | 3 | 0 | 0 | 0 | 0 | 2 |
| 226 | 4 | 4 | 2 | 0 | 0 | 0 | 0 | 9 |
| 140 | 3 | 3 | 1 | 0 | 0 | 0 | 0 | 20 |
| 104 | 4 | 2 | 0 | 0 | 0 | 0 | 0 | 17 |
| 67 | 2 | 2 | 0 | 0 | 0 | 0 | 0 | 6 |
| 64 | 1 | 1 | 1 | 0 | 0 | 0 | 0 | 18 |
| 60 | 1 | 1 | 1 | 0 | 0 | 0 | 0 | 5 |
| 51 | 2 | 1 | 0 | 0 | 0 | 0 | 0 | 24 |
| 50 | 1 | 1 | 0 | 0 | 0 | 0 | 0 | 7 |
| 50 | 2 | 1 | 0 | 0 | 0 | 0 | 0 | 10 |
| 50 | 1 | 1 | 0 | 0 | 0 | 0 | 0 | 19 |
| 46 | 2 | 1 | 0 | 0 | 0 | 0 | 0 | 13 |
| 36 | 1 | 1 | 0 | 0 | 0 | 0 | 0 | 12 |
| 36 | 1 | 1 | 0 | 0 | 0 | 0 | 0 | 25 |
| 33 | 1 | 1 | 0 | 0 | 0 | 0 | 0 | 21 |
| 33 | 1 | 1 | 0 | 0 | 0 | 0 | 0 | 23 |
| 31 | 1 | 1 | 0 | 0 | 0 | 0 | 0 | 11 |
| 16 | 1 | 0 | 0 | 0 | 0 | 0 | 0 | 22 |

FIG. 4

Table 2 : Negative controls ranked in descending order of intensity, taken from a population of 295 negative controls - only 26 controls that gave a signal are listed ie 275 controls were blank.

| Mixture (Mx) | No. observations | Probability |
|---|---|---|
| *Case sample only* | 12105 | 0.8207 |
| *Negative sample only* | 130 | 0.0088 |
| *no sample* | 1345 | 0.0912 |
| <= .1 > 0 | 973 | 0.0660 |
| <= .2 > .1 | 73 | 0.0049 |
| <= .3 > .2 | 30 | 0.0020 |
| <= .4 > .3 | 19 | 0.0013 |
| <= .5 > .4 | 9 | 0.0006 |
| <= .6 > .5 | 9 | 0.0006 |
| <= .7 > .6 | 9 | 0.0006 |
| <= .8 > .7 | 4 | 0.0003 |
| <= .9 > .8 | 6 | 0.0004 |
| <= 1 > .9 | 5 | 0.0003 |
| <= 2 > 1 | 11 | 0.0007 |
| <= 10 > 2 | 19 | 0.0013 |
| <= 25 > 10 | 3 | 0.0002 |
| Total | 14750 | |

FIG. 5

| | Guideline (rfu) | | | | | |
|---|---|---|---|---|---|---|
| Log10 LR | rfu = 50 | rfu = 60 | rfu = 70 | rfu = 80 | rfu = 90 | rfu = 100 |
| 1 | 0.00746 | 0.00502 | 0.00319 | 0.00251 | 0.00339 | 0.00339 |
| 2 | 0.00217 | 0.00095 | 0.00014 | 0.00088 | 0 | 0 |
| 3 | 0.00027 | 0.00041 | 0.00210 | 0 | 0 | 0 |
| 4 | 0.00095 | 0.00183 | 0 | 0 | 0 | 0 |
| 5 | 0.00014 | 0 | 0 | 0 | 0 | 0 |
| 6 | 0.00007 | 0 | 0 | 0 | 0 | 0 |
| 7 | 0.00020 | 0 | 0 | 0 | 0 | 0 |
| 8 | 0.00088 | 0 | 0 | 0 | 0 | 0 |
| 9 | 0 | 0 | 0 | 0 | 0 | 0 |

Table 4: Probability estimates for achieving a given likelihood ratio where a laboratory contaminant is responsible for the major (unmixed) profile.

FIG. 6

Histogram showing probability of a contaminant giving a reportable result (measured as log10 LR) relative to the reporting guideline (currently 50rfu)

ANALYSIS OF DNA

This application is a Divisional Application of U.S. Ser. No. 10/564,682, filed on Jul. 21, 2006, which is a National Stage Application of PCT/GB2004/003003, filed Jul. 9, 2004, which claims benefit of Serial No. 0316519.8, filed Jul. 15, 2003 in the United Kingdom and which applications are incorporated herein by reference. A claim of priority to all, to the extent appropriate is made.

This invention concerns improvements in and relating to the analysis of DNA, particularly, but not exclusively, in relation to the analysis of DNA for use in forensic science. More particularly the invention concerns the provision of information on the chance of contamination and other developments which use that information.

There are a variety of ways in which contaminants can become incorporated in a DNA sample and hence figure in the results. Some such contaminants are address or at least a warning is provided in existing analysis systems. However, such systems do not provide any account for sporadic contamination. The invention has amongst its aims to account thoroughly for such sporadic and undetected contamination; to provide a clear indication as to the potential level of error that may arise from such contamination; to provide guidance as to the threshold at which alternative analysis techniques or protocols should be used; to provide improved methods of operating DNA databases, particularly in terms of additional data which accompanies the DNA profile results reported by organisations to the DNA database operator; and, in particular, to provide a method of estimating the number of false positives for a DNA analysis unit and their associated likelihood ratios.

According to a first aspect of the invention we provide a method of providing information on DNA samples, the method including:— in respect of one or more negative controls, obtaining information on whether or not DNA is suggested as present in the negative controls;

determining the probability of DNA being suggested as present in the negative controls, the determination being based on the number of the negative controls which suggest DNA is present compared with the total number of negative controls considered;

the probability of DNA being indicated as present in the negative control being equated to the probability of the DNA samples being contaminated.

The information on contamination may relate to sporadic contamination and/or undetected contamination.

The contamination may be due to persons involved in the collection and/or handling and/or analysis of the sample. The contamination may be due to the reagents involved in the collection and/or handling and/or analysis of the sample. The contamination may be due to the equipment involved in the collection and/or handling and/or analysis of the sample.

The method may provide information on contamination for the whole or a part of the process between collection of the sample and reporting of the sample. Information may be provided on the overall probability of contamination. Information may be provided on the probability of contamination arising from one or more stages of the overall process. A stage may be the crime scene stage for a sample, for instance between the point before the sample is reached to the point at which the sample is dispatched by the person collecting the sample. A stage may be the evidence recovery unit stage, for instance between the point at which a sample is received at an evidence handling unit and the point at which it is dispatched to an analysis stage. A stage may be an analysis stage, for instance between the point of receipt by the analysis stage and the completion of the DNA profiling of the sample. The analysis stage may be performed by a DNA analysis unit.

The method may provide information on contamination due to one or more elements of the process. An element of the process may extend through one or more of the process stages or may be a feature of a single stage. An element may be the staff involved in the process. This embodiment of the invention may particularly involve the features, options or possibilities set out below in relation to the fifth aspect of the invention, incorporated herein by reference.

Preferably at least 20, more preferably at least 50 and ideally at least 100 negative controls are used.

Preferably the negative controls provide information on the contamination of samples passing through a DNA analysis process above and beyond information on the batch of samples with which the negative control is analysed.

The one or more negative controls may be used to provide information on the contamination for all or part of the process. Preferably the one or more negative controls pass through the stages of the process they are to provide information on the contamination for. Preferably the one or more negative controls pass through the stages of the process they are to provide information for in an equivalent manner to the samples as they pass through those stages of the process. Preferably the manner of collection for a negative control is equivalent to the manner of collection for a sample, but without involving the sample. Preferably the manner of handling of a negative control is equivalent to the manner of handling of a sample. Preferably the manner of analysis of a negative control is equivalent to the manner of analysis of a sample. Preferably the negative controls pass through a crime scene stage in an equivalent manner to samples. Preferably the negative controls pass through an evidence recovery stage in an equivalent manner to samples. Preferably the negative controls pass through an analysis stage in an equivalent manner to the samples.

The one or more negative controls may be used to provide information on the contamination for all elements or an element of the process. Preferably the one or more negative controls interact with the element or elements pass of the process they are to provide information on the contamination for. Preferably the one or more negative controls interact with the element or elements of the process they are to provide information for in an equivalent manner to the samples. Preferably the manner of interaction with the persons involved in one or all stages of the process is the same for a negative control as it is for a sample. Preferably the manner of interaction of a negative control with reagents is the same as it is for a sample. Preferably the manner of interaction of a negative control with equipment is the same as it is for a sample.

Preferably the information on the contamination of DNA samples is provided in respect of a period of time. The period of time may be a fixed period, for instance a month. After the elapse of the time period the method may be repeated. The repeat of the method may provide revised information.

A proportion or, more preferably, all of the negative control samples occurring during a period of time for which information on the contamination is required may be used. Where only a portion of the negative controls are used, preferably these are selected at random. The negative controls used preferably include any for which no DNA is suggested as present.

Preferably the negative controls considered and the samples considered are in respect of the same time period.

The information on the contamination of DNA samples may provided in respect of one or more elements. The elements may be one or more of the people involved with the samples and/or negative controls, the reagents involved with the samples and/or negative controls, the equipment involved with the samples and/or negative controls. After a change in one or more of the elements, for instance a change in equipment supplier, the method may be repeated. The repeat of the method may provide revised information.

A proportion or, more preferably, all of the negative control samples occurring during a set of elements for which information on the contamination is required may be used. Where only a portion of the negative controls are used, preferably these are selected at random. The negative controls used preferably include any for which no DNA is suggested as present.

Preferably the negative controls considered and the samples considered are in respect of the same set of elements.

The information on whether or not DNA is suggested as present in a negative control may include allele position and/or allele length and/or peak area and/or peak height. Preferably DNA is suggested as present where an indication is present which exceeds one or more criteria. Preferably DNA is suggested as not present where an indication is not present or any indication present does not exceed one or more criteria. Preferably equivalent consideration is given to the negative controls as to the samples. Preferably the same characteristics and/or same criteria are used.

Preferably the determination of the probability of DNA being indicated as present in the negative control is the number of negative controls which suggest DNA is present divided by the total number of negative controls.

With respect to a sample, the method may further provide a determination of the probability of a sample suggesting DNA is present in the sample, but that DNA arises from contamination only. This determination may involve, in respect of one or more samples, obtaining information on whether or not DNA is suggested as present in the sample. The number of samples not suggesting DNA is present compared with the total number of samples considered may be assumed to determine the probability of a sample not suggesting DNA as present. The probability of a sample not suggesting DNA as present may be used together with the probability of a negative control being contaminated. The probability of a sample not suggesting DNA as present may be multiplied by the probability of a negative control being contaminated to give the probability of a sample suggesting DNA is present in the sample, but that DNA arises from contamination only.

With respect to a sample, the method may further provide a determination of the probability of a sample suggesting DNA is present in the sample, the DNA arising from the sample and from contamination. This determination may involve, in respect of one or more samples, obtaining information on whether or not DNA is suggested as present in the sample. The number of samples not suggesting DNA is present compared with the total number of samples considered may be assumed to determine the probability of a sample not suggesting DNA as present. The probability of a sample not suggesting DNA as present may be used together with the probability of a negative control being contaminated. The probability of a sample not suggesting DNA as present may be multiplied by the probability of a negative control being contaminated to give the probability of a sample suggesting DNA is present in the sample, but that DNA arises from contamination only. The determination may further involve subtracting the probability of a sample suggesting DNA is present, but that DNA arises from contamination only, from the probability of a negative control being contaminated.

The method may be applied to one or more groups of samples and/or negative controls. A group may be the samples and negative controls from one operating organisation. A group may be the samples and negative controls from one processing line of an operating organisation. The information from the method may be provided to one or more of the subsequent users of the DNA profile or results underlying it, together with the DNA profile or results underlying it. One such subsequent user may be the provider of a DNA database, for instance a database of profiles from known persons and/or from known items or locations and/or from unknown persons. The provider of a DNA database may require the provision of information of the method. Further options and possibilities for this embodiment of the invention are set out in the fourth aspect of the invention below, and are incorporated herein by reference.

The information may be used to assist in defining the format, for instance protocol, followed in a DNA sample analysis process. The DNA sample analysis process may use two or more protocols dependent on one or more variables. The or one of the variables may be the peak height and/or peak area detected for a sample and/or negative control. For instance, where a peak height and/or peak area is detected above a threshold a first protocol may be used in the analysis. For instance, where a peak height and/or peak area is detected at or below a threshold a second protocol may be used. The second protocol may be a low copy number protocol. The second protocol may include analysis of at least duplicate samples of the sample in question. The second protocol may discard the results of the analysis where the first and second analyses of the same sample produce results which are outside of a defined level of similarity. The present threshold for different protocols to be applied is 50 random fluorescence units, 50 rfu.

The information of the present method may be used to determine whether or not the threshold is set at an appropriate level. The present invention may be used to determine the appropriate level for the threshold. Further options, features and possibilities for this embodiment of the invention are set out below in the second and/or third aspects of the invention and they are incorporated herein by reference.

When obtaining information on the negative controls and/or samples peak height and/or peak area and/or allele length and/or allele number may be obtained. In respect of a stage of the process and/or the overall process and/or an element of the process and/or all elements of the process the frequency of occurrence of particular peak heights and/or peak areas may be considered, for instance in relation to small ranges which cover the spread of peak height and/or peak areas encountered. The sum of the peak heights and/or areas may be so considered. The proportion of negative controls which generate peak heights and/or peak areas above the threshold level may be considered. This consideration may provide information as to the level of potential problem contamination for that threshold. This process may be repeated for the threshold and/or one or more revised thresholds. This process may be used to suggest a revised threshold for use in determining which protocol to follow. The revised threshold may be lower than the threshold or may be higher than the threshold. The threshold may be defined in terms of a random fluorescence unit value.

The negative controls may be ranked according to the sum of their peak heights, from highest to lowest. The samples may be ranked according to the sum of their peak heights, from lowest to highest.

The method may include simulating sample DNA and contamination DNA in combination. A plurality of such combinations may be simulated. Preferably each simulated mixture possible, formed of one negative control from amongst the one or more negative controls and one sample from amongst the one or more samples, is simulated. preferably negative controls and/or samples which suggest no DNA present are included amongst the possibilities from which the pairs are generated. Simulations with DNA due only to the sample contribution and/or with DNA due only to the negative control and/or due to both the sample and negative control and/or with no DNA present may be obtained. Preferably the proportions, for instance percentages, of each type of simulation are defined by the probabilities of occurrence of the positions defining those types.

Preferably the simulation includes information on the quantity of DNA present in the simulated mixture due to the sample and due to the negative control. Preferably the simulation includes information on the peak area and/or peak height for DNA present in the simulated mixture due to the sample and due to the negative control.

Where the proportions of the simulations which are negative control DNA only and/or negative control and sample DNA together are above a proportion threshold then the method may include further consideration of at least one or more of those simulation types. The same proportion threshold may be used for each type or different proportion thresholds may be used.

Particularly in respect of simulations which are a mixture of sample DNA and contaminant DNA, but potentially in respect of one or more of the other types too, the following further features of the method may be used. Preferably for one or more of the simulations, potentially all of the simulations, the mixture proportion from the sample and negative control is determined. The mixture proportion may be defined as the sum of the peak height from the negative control divided by the sum of the peak height from the sample. The mixture proportion may be defined as the sum of the peak area from the negative control divided by the sum of the peak area from the sample. The proportion of simulations with a mixture proportion relative to one or more specified levels may be established. The proportion may be those simulations with a negative control contribution >1. The information on mixture proportion may be used to indicate the proportion of cases in which the contamination is the greater part of the mixture and/or is above a level of concern.

Particularly in respect of simulations which are contaminant DNA only, but potentially in respect of one or more of the other types too, the following further features of the method may be used. Likelihood ratios may be calculated for the simulations. The one or more likelihood ratios determined may be the ratio of probabilities where the numerator is the probability of the evidence in the result/DNA profile originating from the suspect and the denominator is the probability of the evidence in the result/DNA profile originating from a random unknown person. Preferably likelihood ratios are only calculated for those simulations in respect of which the peak height and/or peak area, preferably in summed form, is above the threshold applying. Preferably the frequency of occurrence at one or more likelihood ratio levels is calculated with the threshold applying. The threshold applying may be varied to alter the frequency with which a given likelihood ratio occurs. The threshold may be raised to decrease the frequency with which a likelihood ratio occurs and/or to increase the likelihood ratio which occurs with a given frequency. The threshold may be lowered to increase the frequency with which a likelihood ratio occurs and/or to decrease the likelihood ratio which occurs with a given frequency. The thresholds for different operating organisations and/or different processing lines may be adjusted to balance frequency of likelihood ratios between them.

The above method may be used alongside other contamination prevention and/or detection steps, such as the use of elimination databases which contain profiles of staff who could contact the samples and/or negative controls.

The first aspect of the invention may include any of the features, options or possibilities set out elsewhere in this document.

According to a second aspect of the invention we provide a method of providing information on possible errors in a method of analysis, the method of analysis including a threshold which determines the analysis protocol to be applied to the analysis of DNA, the method including:— in respect of one or more negative controls, obtaining information on whether or not DNA is suggested as present in the negative controls;

determining the probability of DNA being suggested as present in the negative controls, the determination being based on the number of the negative controls which suggest DNA is present compared with the total number of negative controls considered;

the probability of DNA being indicated as present in the negative control being equated to the probability of the DNA samples being contaminated;

in respect of one or more DNA samples, obtaining information on whether or not DNA is suggested as present in the DNA sample;

obtaining information about the quantity of DNA in a DNA sample or negative control;

comparing the quantity of DNA in a negative control sample with the threshold to establish the number or proportion of negative controls on one or other side of the threshold.

In this way an indication is provided as to the number of potential false positives which could occur as sufficient contaminant DNA could be present in those cases to give a reportable result.

The method may include adjusting the level of the threshold to alter the number or proportion of negative controls on one or other side of the threshold. The method may include adjusting the level of the threshold to reduce the number or proportion of negative controls above the threshold. In this way the number of potential false positives may also be addressed.

According to a third aspect of the invention, a method of providing information on, in a method of analysis, the likelihood of a result arising due to contamination, the method of analysis including a threshold which determines the analysis protocol to be applied to the analysis of DNA, the method of providing information including:— in respect of one or more negative controls, obtaining information on whether or not DNA is suggested as present in the negative controls;

determining the probability of DNA being suggested as present in the negative controls, the determination being based on the number of the negative controls which suggest DNA is present compared with the total number of negative controls considered;

the probability of DNA being indicated as present in the negative control being equated to the probability of the DNA samples being contaminated;

in respect of one or more DNA samples, obtaining information on whether or not DNA is suggested as present in the DNA sample;

obtaining information about the quantity of DNA in a DNA sample or negative control;

simulating one or more mixtures, the mixtures each being formed from a pairing of a negative control sample and a DNA sample from amongst the one or more negative controls and the one or more DNA samples;

establishing the mixture proportion for one or both of the following types of simulated mixture: DNA from contamination only; DNA from both DNA sample and contamination;

determining a likelihood ratio in respect of a result arising for one or both of the types of simulated mixture.

In this way information quantifying the risk of a false positive is provided.

The following features, options and possibilities may apply to any of the forms of the invention set out in this document, but are particularly applicable to the second and third aspects of the invention.

The information on possible errors may be an indication as to the number of negative controls which contain a quantity of DNA above the threshold. The information on possible errors may be an indication as to the number of contaminated samples which contain DNA above the threshold.

The threshold is preferably a measure of quantity of DNA present. It may be defined in terms of peak area and/or peak height, particularly in respect of a summed value.

Preferably samples above or at and above the threshold are subjected to a first protocol. Preferably samples at and below or below the threshold are subjected to a second protocol. The second protocol may include be a low copy number protocol.

The quantity of DNA may be peak area and/or peak height and/or summed peak area and/or summed peak height.

The simulation may involve simulating each possible pairing of a negative control and sample.

The mixture proportion for one or more of the simulation mixture types: DNA from DNA sample only; no DNA from DNA sample or contaminant may also be established.

A likelihood ratio may be determined in respect of one or both of these mixture types.

Separate likelihood ratios may be determined in respect of one or more of the different simulation mixture types.

A probability of achieving a given likelihood ratio may be determined. Such a determination may be made in respect of one or more likelihood ratio levels and/or may be made in respect of one or more threshold values.

The method may include varying the threshold to give a predetermined likelihood ratio and/or predetermined probability of achieving a likelihood ratio. The method may include varying the threshold to give a likelihood ratio of $>10^3$.

Preferably likelihood ratios are only determined using negative controls and/or samples and/or simulations in which the quantity of DNA is above the threshold in question.

Preferably the method is applied independently to different operating organisations and/or different processing lines within organisations. Different operating organisations and/or different processing lines within organisations may be provided with different thresholds as a result of the method.

The second and/or third aspects of the invention may include any of the features, options or possibilities set out elsewhere in this document.

According to a fourth aspect of the invention we provide a method of operating a database containing information on DNA from samples, the method of operating including:— introducing into the database results from one or more sources;

the operator of the database specifying to the sources that the sources collect information according to a method for providing information on DNA samples, that method including:— in respect of one or more negative controls, obtaining information on whether or not DNA is suggested as present in the negative controls;

determining the probability of DNA being suggested as present in the negative controls, the determination being based on the number of the negative controls which suggest DNA is present compared with the total number of negative controls considered;

the probability of DNA being indicated as present in the negative control being equated to the probability of the DNA samples being contaminated.

The sources may be one or more operating organisations.

The information on DNA samples may be reviewed by the database operator. The database operator may use the information to specify the threshold at which the source uses one or more protocols in their analysis. The database operator may specify a threshold below which the source needs to use a particular protocol, such as a low copy number protocol. The database operator may vary the threshold from time to time, particularly according to variations in the information obtained. The database operator may specify that results from the source may only be introduced onto the database where the threshold is applied and/or where the threshold is applied according to the level specified by the database operator and/or where the information is collected.

The fourth aspect of the invention may include any of the features, options or possibilities set out elsewhere in this document.

According to a fifth aspect of the invention we provide a method of providing information on the contamination of DNA samples by persons involved in the processing of DNA samples, the method including:— determining DNA information of the same type as being analysed for in respect of one or more of the persons involved in processing the DNA samples;

determining the number of samples and/or negative controls contaminated by the one or more persons for whom the DNA information has been determined due to the detection of DNA information corresponding to their DNA information in samples and/or negative controls;

determining the proportion of samples and/or negative controls handled by such persons;

determining the proportion of persons for whom the DNA information has been determined compared with the total number of persons involved in processing the DNA samples.

Preferably the proportion of samples and/or negative controls contaminated is divided by the proportion of persons for whom the DNA information has been determined to give the total proportion of samples and/or negative controls contaminated by the total number of persons involved in the processing of the DNA samples. The method may be applied to one or more stages of the overall process. The method may be applied to the overall process. The calculation for the overall process may consider the cumulative effect of different stages. This may involve the consideration of different apparent contamination rates and different proportions of persons for whom the DNA information has been determined for different parts and/or stages of the process.

The fifth aspect of the invention may include any of the features, options or possibilities set out elsewhere in this document.

According to a sixth aspect of the invention we provide a method of determining the threshold to be used within a method of analysis by an operating organisation to determine which analysis protocol to apply, the method including:— setting a threshold;

determining the likelihood ratio for false positives for that operating organisation with that threshold;

adjusting the value of the threshold ensure false positives do not exceed a desired likelihood ratio.

The sixth aspect of the invention may include any of the features, options or possibilities set out elsewhere in this document.

According to a seventh aspect of the invention we provide a method of analysing DNA samples, the method including the analysis of negative controls to provide information on the contamination of DNA samples, wherein, in respect of at least one sample, a negative control arises at the point of the DNA samples collection and is treated in the same manner between that point and the conclusion of the analysis method.

The seventh aspect of the invention may include any of the features, options or possibilities set out elsewhere in this document.

The invention will now be described, by way of example only, and with reference to the accompanying drawings in which:

FIG. 3 is a table presenting case samples ranked in order of increasing summed peak height with numbers of alleles scored above a given peak height;

FIG. 4 is a table illustrating negative controls ranked in descending order of intensity, taken from a population of 295 negative controls;

FIG. 5 is an analysis of a number of observations in respect of varying relative mixture forms;

FIG. 6 is a table setting out probability estimates for achieving a given likelihood ratio where a laboratory contaminant is responsible for the major (unmixed) profile.

All techniques are subject to potential sources of error. When analysing DNA samples to establish the DNA profile, a number of steps are taken to prevent contamination by other DNA.

Attempts are also made to identify instances in which contamination is occurring. Such steps include the use of "elimination databases" which contain profile information relating to the operators involved in the analysis process so as to allow for the identification of results in which the operator contaminates the sample. The techniques also include detection of potential cross contamination between one sample and another being processed concurrently. This may occur where there is lane to lane leakage within the analysis process, for instance.

Sporadic and undetected contamination of samples can still occur and could potentially give rise to results which in turn lead to false positives. Thompson et al (2003) J. Forensic Sci. 48, 47-54 has recently suggested that false positives can dramatically reduce the value of DNA evidence, especially when the priors odds that the suspect is the source of an evidence sample are low. Such a situation occurs when a DNA database is "trawled" to search for "cold hits", for instance.

The present invention seeks to account thoroughly for such sporadic and undetected contamination; to provide a clear indication as to the potential level of error that may arise from such contamination; and to provide guidance as to the point at which alternative analysis techniques or protocol should be used. The present invention also seeks to provide improved methods of operating DNA databases, particularly in terms of additional data which accompanies the DNA profile results reported by organisations to the DNA database operator. In particular, the invention seeks to provide a method of estimating the number of false positives for a DNA analysis unit and their associated likelihood ratios.

Figure 1:
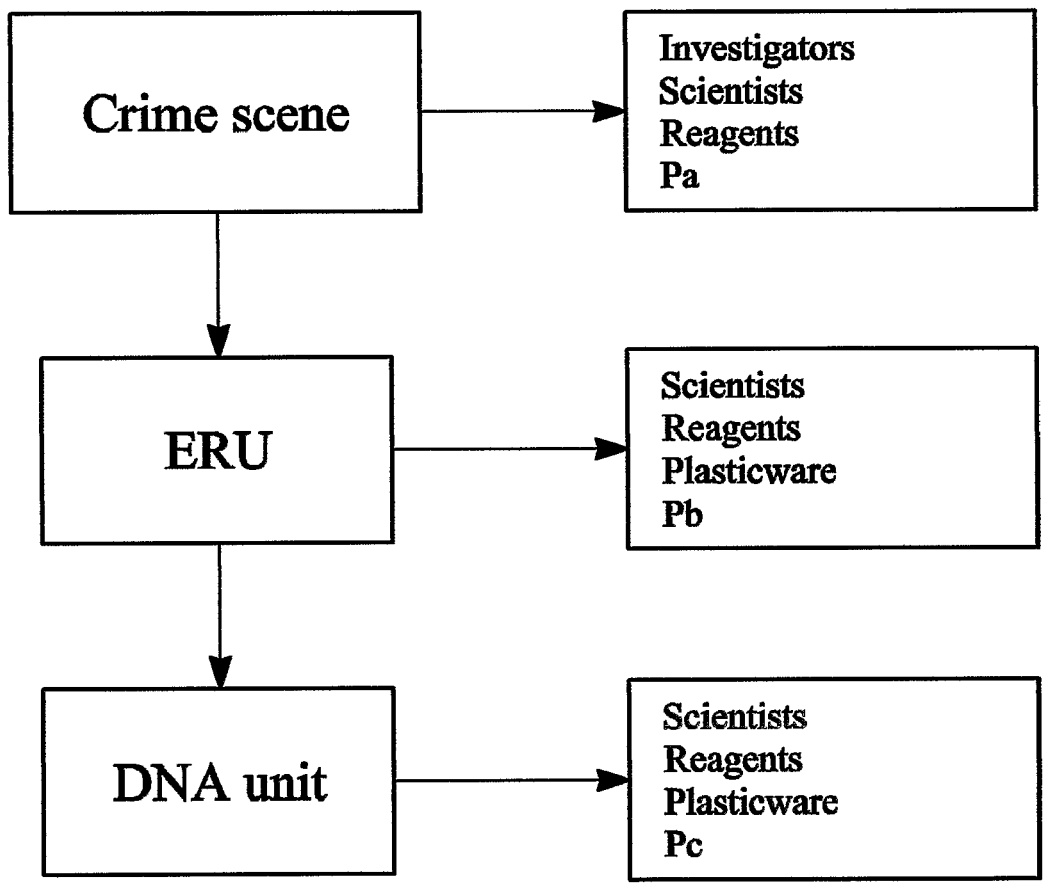
FIG. 1 is an illustration of the potential origin of contaminants.

Referring to FIG. 1, the entire process involved in the collection, handling, processing and reporting DNA samples is illustrated. Within this overall process, three discrete categories for the origins of contamination can be identified.

Firstly, contamination can arise at the crime scene. This may be due to contamination by the investigating officers and/or by the reagents and/or equipment they use to collect evidence. This probability of contamination is denoted Pa.

Secondly, when the collected sample is transferred to the evidence recovery unit, ERU, again contamination may arise from the scientists involved and/or the reagents and/or equipment they use. The probability of contamination from this part of the process is denoted Pb.

Thirdly, within the DNA analysis unit, there is also potential contamination from scientists and/or their reagents and/or equipment. The probability of contamination here is denoted Pc.

As contaminants can pass from crime scene to ERU to the DNA analysis unit, at each stage there is an additional opportunity for contamination to occur. As a result the contamination process is additive, and the chances of contamination can be summarised as equal to Pa+Pb+Pc.

Within DNA analysis units, negative controls are presently used. These are samples, generated and analysed within the DNA analysis unit, which are assumed to be DNA free. At present when a reportable DNA profile is observed in such a negative control, the batch of samples is eliminated from further consideration due to suspected contamination of all.

Recent investigations by the applicant indicate that this is not necessarily an appropriate course of action, and may not address the issue, as most, if not all, contamination events seen in negative controls are sporadic single tube events. As the contaminant is specific to one tube only, this means that it is unlikely that the contamination detected for that tube will have any relevance to the associated batch of extracted samples being processed.

The present invention seeks to use negative controls in a fundamentally different way. Instead of using them as indicative of issues with the batch they form a part of, the present invention uses negative controls in relation to the entire DNA process of a DNA analysis unit. This is possible because negative controls are processed in the same way as samples of interest, such as casework samples. Hence they can be used to estimate the level of contamination in casework samples over the same period of time.

Whilst the invention is initially described below in relation to negative controls generated in the DNA analysis unit, and hence reflecting the impact of the DNA analysis unit on the process, it would be beneficial to use negative controls which reflect the entire process and this is recommended. Thus, negative controls could be generated at the crime scene, passed through the ERU stage and passed through the DNA analysis unit. Negative controls in those circumstances would reflect the potential contamination arising from all stages in the process. This might for instance involve the use of a moistened swab to collect evidence at a crime scene, with an additional blank swab also being moistened with water at the crime scene. Both would then be passed to the ERU in the same way, handled and then passed on to the DNA analysis unit in the same way. Both samples would then be analysed in the same way within the DNA analysis unit. As a result an estimate of Pa+Pb+Pc would be obtained. The technique is described in more detail below in relation to estimating Pc only.

To obtain the benefits of the invention for a DNA unit it is desirable to obtain a significant number of negative controls over a time period for which an assessment is being made and also obtain a number of casework DNA profiles from the same time period. The casework DNA profiles may be a random selection from amongst all the casework profiles conducted during the time period. Samples that failed to give any signal should be included. Ideally all of the negative controls run during the time period are included, including those samples for which no signal is obtained.

In a specific example relating to one analysis unit, 295 negative controls were obtained covering a five month period. A random collection of 50 casework DNA profiles obtained during the same period was also taken.

Out of the 50 casework samples analysed, 5 failed to give a result. The probability of the DNA unit sample failing to give any profile, Pf, therefore=5/50=0.1.

Out of the 295 negative controls analysed, a total of 26 samples gave a signal. This means that the probability of a negative control giving a profile of one or more alleles, Pn=26/295=0.088.

Contamination is only detected or known to have occurred if it is found in a negative control tube purported to be free of DNA. The difficulty is that it is not possible to assess directly whether a casework sample is affected by sporadic contamination, as there is no supporting information. However, even though we cannot know which particular casework tube is contaminated, we can assess the probability, $P_C$, of any given tube being affected, because negative samples are simply a subset of casework samples. They are treated in exactly the same way as casework samples within the DNA analysis unit and hence are subject to the same contamination rates. The probability of the casework sample being contaminated is the same as the probability that a negative control is contaminated (where the contamination may be 1+ alleles). And so:—

$$P_N = P_C = 0.088$$

If a casework sample is contaminated then this will result in one of two different outcomes:

a. If the casework sample is devoid of DNA then only the contaminant will be visible and the profile is unmixed. The chance of this occurrence ($P_S$)) is the probability of contamination multiplied by the probability of a DNA unit sample failing to give a profile:—

$$P_S = P_N \times P_F$$

Specifically, in relation to the actual results for the unit described above, this gives $P_S=0.088 \times 0.1=0.009$ (or approximately 0.9% of samples will be contaminated and the profile does not appear admixed).

b. If the casework sample includes sample DNA and contaminant DNA then there is no way of discerning this from casework samples merely containing sample DNA. However, the chance of this occurrence is:—

$$P_N - P_S$$

Thus, in relation to the actual results of the DNA unit described above, $P_N - P_S = 0.088 - 0.0088 = 0.079$ (or 7.9%) of casework samples which contain sporadic contamination in admixture with a case-work profile.

This analysis gives important information about the likelihood of sporadic contamination occurring for a particular DNA analysis unit. A similar analysis process applied to different DNA units will potentially reveal different likelihoods depending on the procedures, equipment and staff present at that DNA unit. It is envisaged that because DNA databases receive results from a plurality of different DNA analysis units, that each DNA analysis unit would be required by the DNA database operator to provide this information to allow false positive risk calculations to be performed. This requirement could extend as far as DNA analysis units of different operating organisations, or to different DNA analysis units whether operated by the same or different operating organisations.

Whilst the above calculations indicate that sporadic contamination will affect samples on a regular basis, and so provide useful guidance on that issue, they do not give an indication of the actual impact to casework reporting. For instance, if the contaminant alleles are all sub-50 rfu (random fluorescence units) in terms of the results they produce then this is below the level set by the present Low Copy Number, LCN, guidelines. Potential techniques for use as an LCN analysis protocol are detailed in WO01/79541, and Gill et al Forensic Sci. Int 112 (2000) 17-40, the contents of which are incorporated herein by reference. As a result an LCN analysis protocol would be used to ensure that the samples are subjected to a more rigorous consideration. In most cases that will ensure they are not reported because the protocol followed in such cases is to perform duplicate analysis of the sample, and not to consider the results where the results of the two samples are insufficiently similar to one another. It is very unlikely that equivalent contamination will occur to both samples in such cases, and as a result the contamination will not be duplicated between the two samples.

Figure 2:
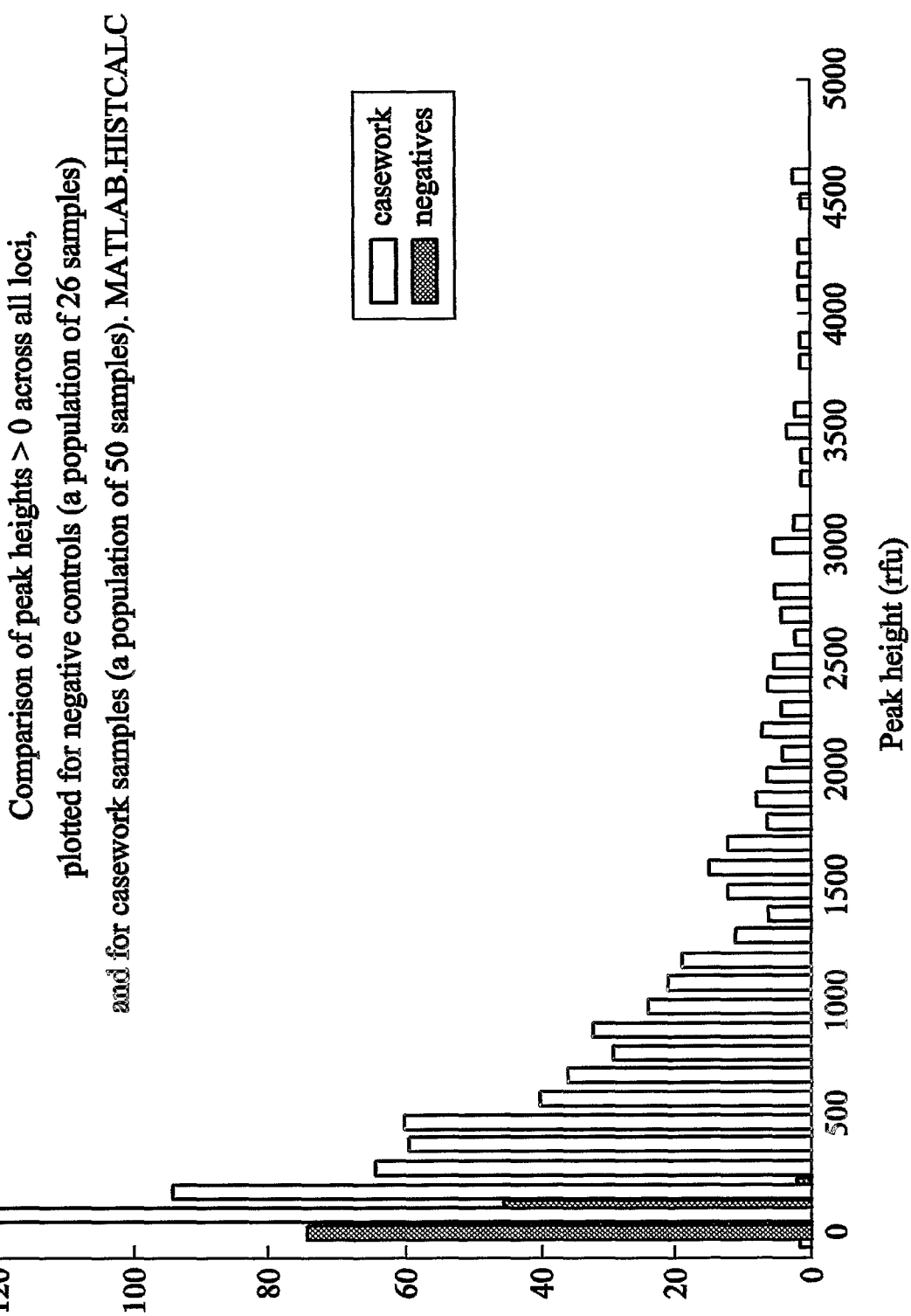
FIG. 2 is a plot of a number of occurrences against the height for negative controls and for casework samples.

To continue the assessment of the impact of this contamination rate it is necessary to evaluate negative control and casework data in much greater detail with special emphasis on their relative peak areas and heights. To do this, peak heights of all data are combined. The results of this combination and are plotting in relation to the above mentioned experimental results. This information is illustrated in FIG. 2. MATLAB. HISTCALC was used to process the data. Note that for bigger data sets a more complete analysis could be achieved using separate individual loci.

The analysis of FIG. 2 reveals that the majority, 58%, of the contaminant peak heights from the negative controls which reported DNA profiles are <50 rfu. As such these should be handled effectively by existing LCN protocols and so not give false positive's. However, 42% of the negative control samples give peak heights >50 rfu. These would not be subjected to LCN protocols as DNA analysis units presently operated with a 50 rfu level according to the LCN guidelines. Consequently, there is overlap between negative control samples with DNA profiles reporting, and casework samples with DNA profiles reporting in the peak height up to approximately 150 rfu range. Consideration of the casework information presented in FIG. 2 indicates that approximately 17% of alleles are to be found reporting in the >50<100, with approximately 70% of casework data having <250 peak height. A significant proportion of negative controls, therefore, fall within the range in which the present sub-50 rfu threshold would not lead to LCN protocols being applied. As a consequence the duplicate sample verification would not assist in this area.

Again whilst this information on the issue is useful, the invention can provide further benefit. Given that in a significant number of instances casework sample only DNA, negative control only DNA and DNA from both casework sample and negative control could report to the results the potential for a misleading result in the subsequent analysis stage is now discussed.

A MATLAB program (NEGSIMPROG) was used to rank the sum of peak heights of weakest→strongest casework samples, the table of FIG. 3, and strongest→weakest negative controls, the table of FIG. 4, respectively. The worst scenario, in terms of potential problems, is where a strong contaminant DNA signal combines with a weak or absent casework sample DNA signal. To determine the extent to which such combinations occur it is necessary to simulate such occurrences and their impact. To do this mixtures were simulated by MATLAB.MIXSIMULATOR using pairwise combinations of casework sample v. negative control (including all examples where profiles were absent). This means that from 50 casework samples and 295 negative controls, pairwise combinations generate 50×295=14750 mixtures.

The simulated results arising comprise the following types, and form the indicated proportion of the 14750 mixtures:—
  Unmixed case samples only (82%)
  Unmixed contamination (0.9%)
  A mixture of case sample and contaminant (7.9%)
  No DNA profile detected (9.1%)

In respect of the 82% of samples which were casework sample only DNA and the 9.1% of samples which contain no DNA there is no problem.

In respect of the 7.9% in the form of a mixture of casework sample DNA and contaminant DNA, the mixture proportion (Mx) was calculated as Mx=sum peak heights contaminant/sum peak heights casework samples. The distribution of Mx is given in the table of FIG. 5. Most mixtures gave Mx<1 which means that the casework sample was the major component. In approximately 1 in 500 cases the major component was the laboratory contaminant, in the most extreme example Mx=25. However, this analysis reveals that the chances of a false result in the case of DNA from sample and contamination is very low as only in 0.2% of the cases is the contamination of a high enough level to run the risk of a false positive. By far and away the more significant risk comes from the 0.9% of cases where only contaminant DNA is present (of course the investigators do not know this is the source compared with the sample being the source).

Figure 7:
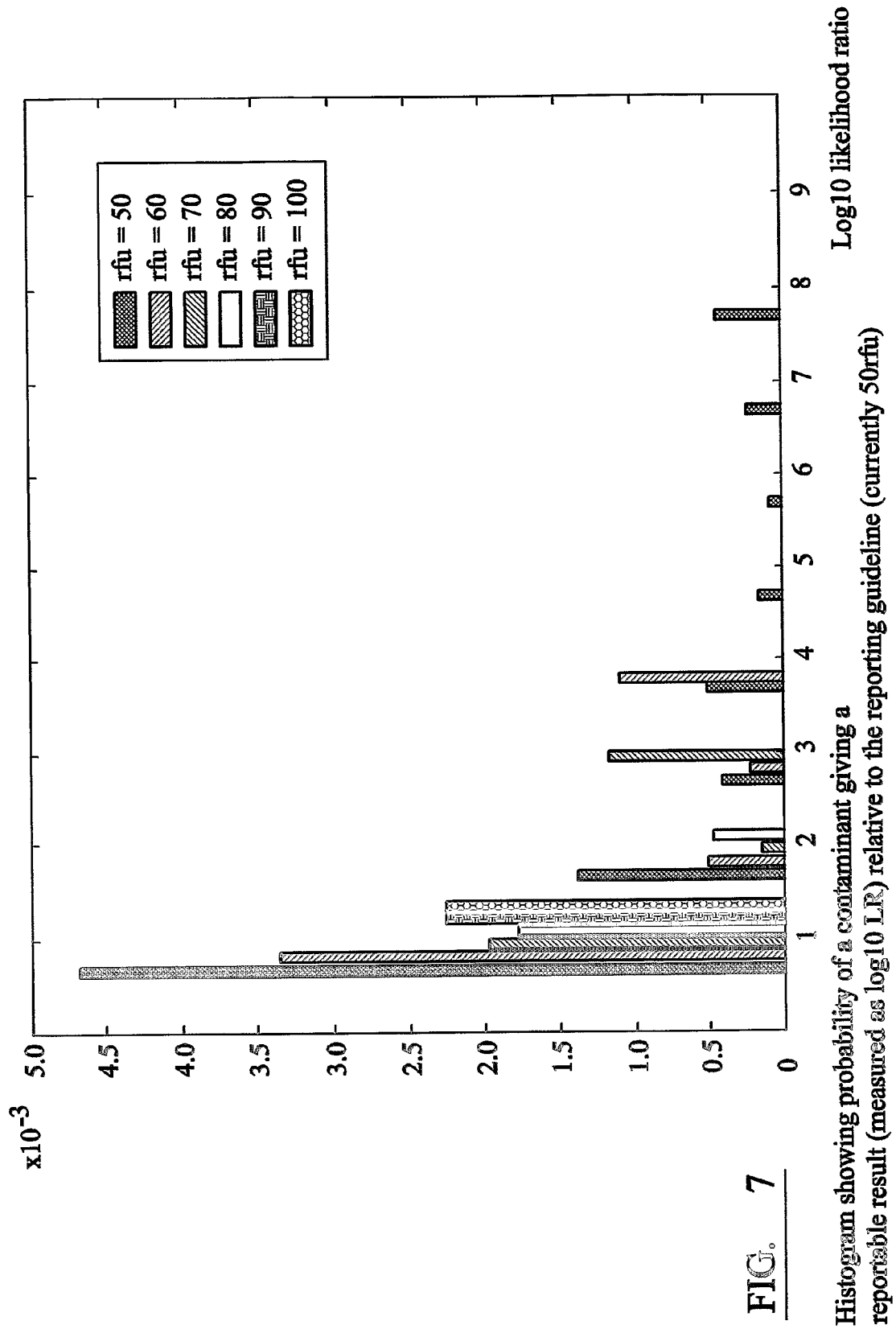
FIG. 7 is a histogram plot showing probability of a contaminant giving a reportable result (measured as log 10 LR) relative to the reporting guideline.

Having obtained this useful indication that a significant number of situations arise in which contamination is the only component, the impact of this upon casework reporting and in terms of the impact upon any database results are loaded into or used against is considered. As cases are reported in terms of likelihood ratios, the MATLAB.MIXSIMULATOR was used to calculate the likelihood ratios of DNA profiles that originated from contamination only. Following the previously mentioned LCN guidelines, alleles were not incorporated in calculations unless above the LCN threshold which is 50 rfu. Only unmixed contaminants are collated into the table of FIG. 6. The likelihood ratios are the ratio of probabilities where the numerator is the probability of the evidence if the DNA profile originated from the suspect and the denominator is the probability of the evidence if the DNA profile originated from a random unknown person. The chance of a laboratory contaminant resulting in a reportable profile with the indicated likelihood ratios is expressed not only with rfu=50 but also with higher rfu thresholds; below the level a LCN protocol is applied. With an rfu of 50 and an $LR>10^7$ the chance of a laboratory contaminant resulting in a reportable profile was approximately 1 in 1000. Higher rfu thresholds had a marked effect on the chance of contaminants resulting in a reportable profile with such an LR. FIG. 7 provides a graphical representation of the results.

The above mentioned investigation reveals the importance of the rfu threshold set by the LCN guidelines at which a LCN protocol cuts in being set at the appropriate level for a DNA analysis unit for any particular period of time. If the rfu threshold is at an appropriate level then a LCN protocol will be applied to interpret the majority of cases which could otherwise give rise to problems. If the LCN threshold is set too low, then a significant number of cases may be processed outside of a LCN protocol, even though such a protocol would be more appropriate so as to address the risk of contamination making a meaningful contribution to the DNA profile determined.

Just as it is perfectly possible for the technique to establish that different DNA analysis units will need a different LCN threshold, it is perfectly possible that the threshold could change between different time periods for a given DNA analysis unit. Thus periodic reevaluation of the threshold is advisable. Changes in procedure, reagent characteristics, equipment characteristics and the like could all cause variations with time. Similarly, if the negative controls account for the crime scene and ERU contaminant contributions as well, variations in the applicable threshold may also arise over time. The technique described has been illustrated with reference to an example used for accounting for any contamination within the DNA analysis unit. It would be possible for differences in contamination arising from different crime scene types, different crime scene officers, different ERU units and the like to be considered separately, or more preferably, to monitor contamination as a whole within the entire sequence of steps.

In an example of one such quantification of the risk of contamination from one part of the operation, the present invention can be used to quantify the chance of contamination from scientists involved in the same part of the process as those whom have already submitted their profile to an elimination database. The same part of the process could be the DNA analysis unit part of the process.

To establish the chance of contamination occurring in this part of the process the number of instances of contamination from a person included in the elimination database is noted. This number of occasions can be used together with knowledge of the proportion of people who are included in the elimination database to quantify the overall chance. Thus if one third of the samples were handled by scientists on the elimination database and 0.01% of the overall samples handled were determined to be contaminated by these people, the overall level of contaminated samples would be 0.03%.

The invention claimed is:
1. A method of providing information on the contamination of DNA samples by persons involved in the processing of the DNA samples, the processing of the DNA samples being applied to a number of samples and a number of negative controls, the processing of the DNA samples involving one or more persons, the processing of the DNA samples including defining a type of DNA information being analysed for and analysing for variation within the type of DNA information;
  the method of providing information on the contamination of the DNA samples including:
  a) determining the variation within the type of DNA information being analysed for in respect of a selected person from amongst the one or more of the persons involved in the processing of the DNA samples;
  b) determining the number of the samples and/or the negative controls contaminated by the selected person for whom the type of DNA information has been determined in step a) due to the detection of the variation within the type of DNA information corresponding to their variation within the type of DNA information in the samples and/or the negative controls;

c) determining what proportion of the samples and/or the negative controls are handled by the selected person.

2. A method according to claim 1 in which the proportion of samples and/or negative controls contaminated is divided by the proportion of persons for whom the DNA information has been determined to give the total proportion of samples and/or negative controls contaminated by the total number of persons involved in the processing of the DNA samples.

3. A method according to claim 1 in which the method is applied to one or more stages of the overall process.

4. A method according to claim 3 in which the one or more stages are selected from a group including: a collection stage, a handling stage, an analysis stage, a crime scene stage, an evidence recovery unit stage.

5. A method according to claim 1 in which the method is applied to the overall process.

6. A method according to claim 5 in which the overall process is between the point of receipt by an analysis stage and completion of DNA profiling of the DNA sample.

7. A method according to claim 1 in which step a) provides one or more determinations and the one or more determinations provide content for an elimination database.

8. A method according to claim 1 in which the information on contamination of the DNA samples is provided in respect of a fixed period of time and after elapse of the period of time the method is repeated and revised information is provided and used.

9. A method according to claim 1 in which the information on contamination of the DNA samples is used to assist in defining a format followed in a DNA sample analysis process.

10. A method according to claim 9 in which the format followed in the DNA sample analysis includes analysis up to completion of DNA profiling of the DNA sample.

11. A method of providing information on the contamination of DNA samples by persons involved in the processing of the DNA samples, the processing of the DNA samples being applied to a number of samples and a number of negative controls, the processing of the DNA samples involving one or more persons, the processing of the DNA samples including defining a type of DNA information being analysed for and analysing for variation within the type of DNA information; the method of providing information on the contamination of the DNA samples including:
a) determining the variation within the type of DNA information being analysed for in respect of a selected person from amongst the one or more of the persons involved in the processing of the DNA samples;
b) determining the number of the samples and/or the negative controls contaminated by the selected person for whom the type of DNA information has been determined in step a) due to the detection of the variation within the type of DNA information corresponding to their variation within the type of DNA information in the samples and/or the negative controls;
c) determining what proportion of the samples and/or the negative controls are handled by the selected person;
d) determining the proportion of the one or more persons involved in the processing of the DNA samples for whom the variation within the type of DNA information has been determined compared with a total number of persons involved in the processing of the DNA samples.

12. A method according to claim 11 in which the proportion of samples and/or negative controls contaminated is divided by the proportion of persons for whom the DNA information has been determined to give the total proportion of samples and/or negative controls contaminated by the total number of persons involved in the processing of the DNA samples.

13. A method according to claim 11 in which the method is applied to one or more stages of the overall process.

14. A method according to claim 13 in which the one or more stages are selected from a group including: a collection stage, a handling stage, an analysis stage, a crime scene stage, an evidence recovery unit stage.

15. A method according to claim 11 in which the method is applied to the overall process.

16. A method according to claim 15 in which the overall process is between the point of receipt by an analysis stage and completion of DNA profiling of the DNA sample.

17. A method according to claim 11 in which step a) provides one or more determinations and the one or more determinations provide content for an elimination database.

18. A method according to claim 11 in which the information on contamination of the DNA samples is provided in respect of a fixed period of time and after elapse of the period of time the method is repeated and revised information is provided and used.

19. A method according to claim 11 in which the information on contamination of the DNA samples is used to assist in defining a format followed in a DNA sample analysis process.

20. A method according to claim 19 in which the format followed in the DNA sample analysis includes analysis up to completion of DNA profiling of the DNA sample.

21. A method of providing information on the contamination of DNA samples by persons involved in the processing of DNA samples, the method including:
a) determining DNA information of the same type as being analysed for in respect of one or more of the persons involved in processing the DNA samples;
b) determining the number of samples and/or negative controls contaminated by the one or more persons for whom the DNA information has been determined due to the detection of DNA information corresponding to their DNA information in samples and/or negative controls;
c) determining the proportion of samples and/or negative controls handled by such persons;
d) determining the proportion of persons for whom the DNA information has been determined compared with the total number of persons involved in processing the DNA samples.

22. A method according to claim 21 in which the proportion of samples and/or negative controls contaminated is divided by the proportion of persons for whom the DNA information has been determined to give the total proportion of samples and/or negative controls contaminated by the total number of persons involved in the processing of the DNA samples.

23. A method according to claim 21 in which the method is applied to one or more stages of the overall process.

24. A method according to claim 23 in which the one or more stages are selected from a group including: a collection stage, a handling stage, an analysis stage, a crime scene stage, an evidence recovery unit stage.

25. A method according to claim 21 in which the method is applied to the overall process.

26. A method according to claim 25 in which the overall process is between the point of receipt by an analysis stage and completion of DNA profiling of the DNA sample.

27. A method according to claim 21 in which step a) provides one or more determinations and the one or more determinations provide content for an elimination database.

28. A method according to claim 21 in which the information on contamination of the DNA samples is provided in respect of a fixed period of time and after elapse of the period of time the method is repeated and revised information is provided and used.

29. A method according to claim 21 in which the information on contamination of the DNA samples is used to assist in defining a format followed in a DNA sample analysis process.

30. A method according to claim 29 in which the format followed in the DNA sample analysis includes analysis up to completion of DNA profiling of the DNA sample.

* * * * *